United States Patent
Takakura et al.

(10) Patent No.: US 8,783,902 B2
(45) Date of Patent: Jul. 22, 2014

(54) ILLUMINATING DEVICE

(75) Inventors: Junya Takakura, Tokyo (JP); Yoshie Imai, Tokyo (JP); Toshimitsu Kaneko, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 140 days.

(21) Appl. No.: 13/561,397

(22) Filed: Jul. 30, 2012

(65) Prior Publication Data

US 2013/0039053 A1    Feb. 14, 2013

(30) Foreign Application Priority Data

Aug. 12, 2011  (JP) .................................. 2011-176983

(51) Int. Cl.
*F21V 9/00* (2006.01)
*H05B 37/02* (2006.01)

(52) U.S. Cl.
USPC ........... 362/231; 362/800; 362/545; 362/555; 315/297; 315/308

(58) Field of Classification Search
USPC ......... 362/231, 230, 235–239, 249, 227, 295, 362/545, 555, 601, 800; 315/246, 149, 397, 315/294, 308
See application file for complete search history.

(56) References Cited

U.S. PATENT DOCUMENTS

| | | | |
|---|---|---|---|
| 6,577,073 B2 * | 6/2003 | Shimizu et al. | ............... 315/246 |
| 6,817,735 B2 * | 11/2004 | Shimizu et al. | ............... 362/231 |
| 7,008,078 B2 * | 3/2006 | Shimizu et al. | ............... 362/231 |
| 7,656,371 B2 * | 2/2010 | Shimizu et al. | ................. 345/83 |
| 7,939,794 B2 * | 5/2011 | Rains et al. | ................... 250/228 |
| 8,222,584 B2 * | 7/2012 | Rains et al. | ................... 250/205 |
| 8,525,444 B2 * | 9/2013 | Van Duijneveldt | ........... 315/308 |
| 2010/0060195 A1 | 3/2010 | Tsuboi et al. | |
| 2010/0063566 A1 | 3/2010 | Uchiumi et al. | |
| 2013/0328501 A1 * | 12/2013 | Moriuchi et al. | ............. 315/294 |

FOREIGN PATENT DOCUMENTS

| | | |
|---|---|---|
| JP | 2000156102 | 6/2000 |
| JP | 2008251337 | 10/2008 |
| JP | 2010238407 | 10/2010 |
| WO | 2008/069101 | 12/2008 |
| WO | 2008/069103 | 12/2008 |

OTHER PUBLICATIONS

Office Action mailed Apr. 30, 2014 in counterpart Japanese Patent Application No. 2011-176983 and English translation thereof.

\* cited by examiner

*Primary Examiner* — Vibol Tan
(74) *Attorney, Agent, or Firm* — Nixon & Vanderhye, P.C.

(57) ABSTRACT

In an embodiment, an illuminating device includes a light source, a light source control unit, an estimation unit, a first calculating unit, and a second calculating unit. The light source includes light emitters, each having a different spectral distribution. The light source control unit determines an emission intensity of each of the light emitters. The estimation unit estimates a spectral reflectivity of an object. The first calculating unit calculates a first evaluation value, indicating an adequacy of a color of the object visually perceived, based on the spectral distributions and the spectral reflectivity. The second calculating unit calculates a second evaluation value, indicating how much an influence is given by the illuminating light to factors other than a visual sense. The light source control unit determines the emission intensities by which the first evaluation value and the second evaluation value satisfy a restraint condition determined beforehand.

8 Claims, 7 Drawing Sheets

ILLUMINATING DEVICE

CROSS-REFERENCE TO RELATED APPLICATION(S)

This application is based upon and claims the benefit of priority from Japanese Patent Application No. 2011-176983, filed on Aug. 12, 2011; the entire contents of which are incorporated herein by reference.

FIELD

Embodiments of the present invention relate generally to an illuminating device.

BACKGROUND

It has been known that illuminating light is incident on a human's retina, and then, acts on a region called suprachiasmatic nucleus through a retinohypothalamic tract to thereby exert not only visual influence but also physiological influence. It has also been known that this effect is especially high in light having a lot of short-wavelength lights near 460 nm. For example, it is pointed that exposure to illuminating light at night inhibits secretion of hormone that is melatonin, which may affect a sleep quality. Therefore, a reduction of such influence has been demanded for the illumination used at night.

In order to reduce the influence, it is considered that the illuminating light does not contain light near 460 nm. However, this undesirably deteriorates color rendering properties that are significant functions for the illumination. The color rendering properties are an index indicating how close a color appearance of an object under a certain illumination is to a color appearance of the object under a standard light source. The measurement of the color rendering properties is specified under Japanese Industrial Standards JIS Z8726.

Evaluation methods of the color rendering properties include a general color rendering index and a special color rendering index. The general color rendering index is obtained by calculating color appearances of 8 colors, each having middle level of brightness and vividness, and having a whole hue. The special color rendering index is obtained by calculating color appearances of 15 colors, which include, in addition to 8 colors used for the general color rendering index, colors that reproduce a color and skin color more vivid than those of 8 colors. These values can be calculated by a value of a spectral distribution of the illuminating light.

There has been known a technique of reducing a non-visible influence of illumination with color rendering properties being kept beyond a certain level by solving an optimization problem of minimizing a value of melatonin secretory inhibiting amount under a restraint condition such that the value of the color rendering index is kept beyond a certain level.

However, in the related art, even when an object that does not reflect light near 460 nm is illuminated, for example, light near 460 nm has to be contained in a certain level in order to keep the value of the color rendering index beyond a certain level. Specifically, light with a wavelength unnecessary for keeping a color appearance of an object is contained, resulting in that the non-visual influence cannot efficiently be reduced.

DETAILED DESCRIPTION

In an embodiment, an illuminating device includes a light source, a light source control unit, an estimation unit, a first calculating unit, and a second calculating unit. The light source includes light emitters, each having a different spectral distribution. The light source control unit determines an emission intensity of each of the light emitters. The estimation unit estimates a spectral reflectivity of an object to which illuminating light is irradiated. The first calculating unit calculates a first evaluation value, indicating an adequacy of a color of the object visually perceived, based on the spectral distributions and the spectral reflectivity. The second calculating unit calculates a second evaluation value, indicating how much an influence is given by the illuminating light to factors other than a visual sense, based on the spectral distribution. The light source control unit determines the emission intensities by which the first evaluation value and the second evaluation value satisfy a restraint condition determined beforehand.

Preferable embodiments of an illuminating device will be described in detail below with reference to the attached drawings.

First Embodiment

The illuminating device according to the first embodiment prevents light with a wavelength unnecessary for keeping a color appearance of an object from being contained in illuminating light, thereby efficiently reducing non-visual influence.

Figure 1:
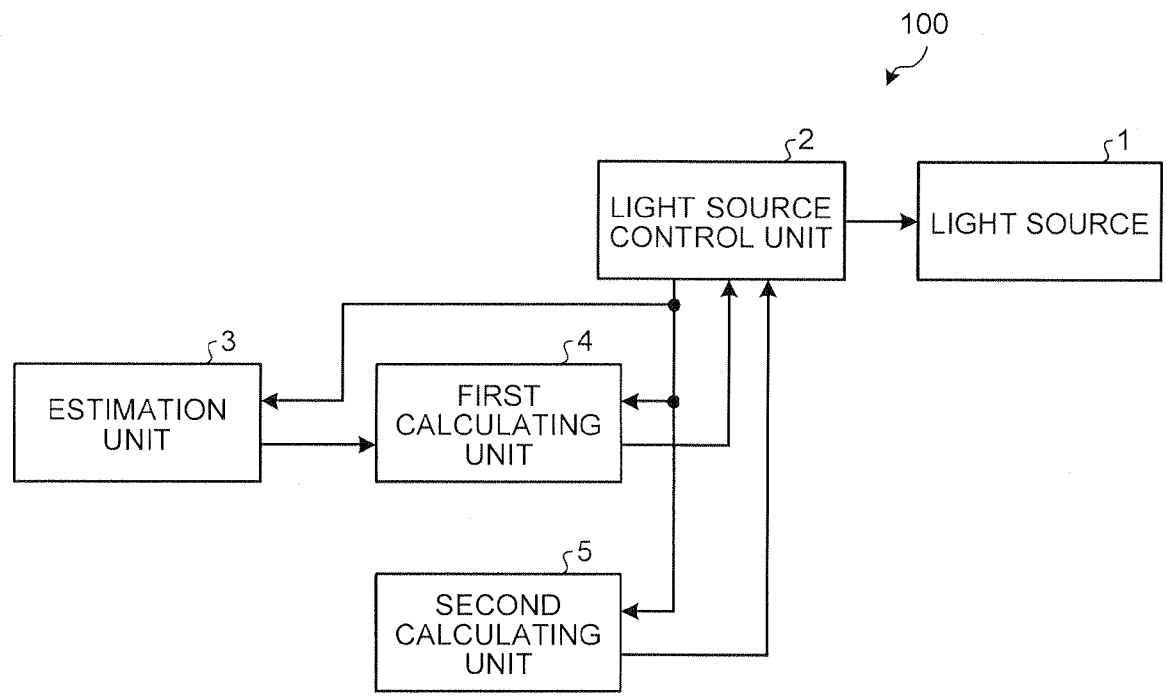
FIG. 1 is a block diagram illustrating an illuminating device according to a first embodiment.

FIG. 1 is a block diagram illustrating one example of a configuration of an illuminating device 100 according to the first embodiment. As illustrated in FIG. 1, the illuminating device 100 includes a light source 1, a light source control unit 2, an estimation unit 3, a first calculating unit 4, and a second calculating unit 5.

The light source 1 is configured to independently control emission intensity, and include two or more types of light emitters, each of which has different spectral distribution. The light emitters are typically LEDs (Light Emitting Diode) corresponding to three primary colors of RGB.

The LED is compact, and light-weight. Therefore, it is relatively easy to incorporate plural LEDs into one illuminating device, and to control the emission intensity of each LED independently.

When the spectral distribution of each LED is defined as $P_i(\lambda)$, and the emission intensity of each LED is defined as $a_i$, the spectral power distribution $P(\lambda)$ as the whole illuminating device having incorporated therein n types of LEDs, each having a different spectral distribution, can be represented by Equation (1) described below.

$$P(\lambda) = \sum_{i=1}^{n} a_i P_i(\lambda) \quad (1)$$

Specifically, the spectral power distribution of the light source 1 can be considered to be a value of a function determined by n-dimensional vectors $A=(a_1\ a_2\ a_3\ \ldots\ a_n)$.

A value of the color rendering index and a value of melatonin secretory inhibiting amount can be calculated, if the spectral distribution is found. Therefore, if a value of n-dimensional vector A is determined, these can be calculated.

Figure 2:
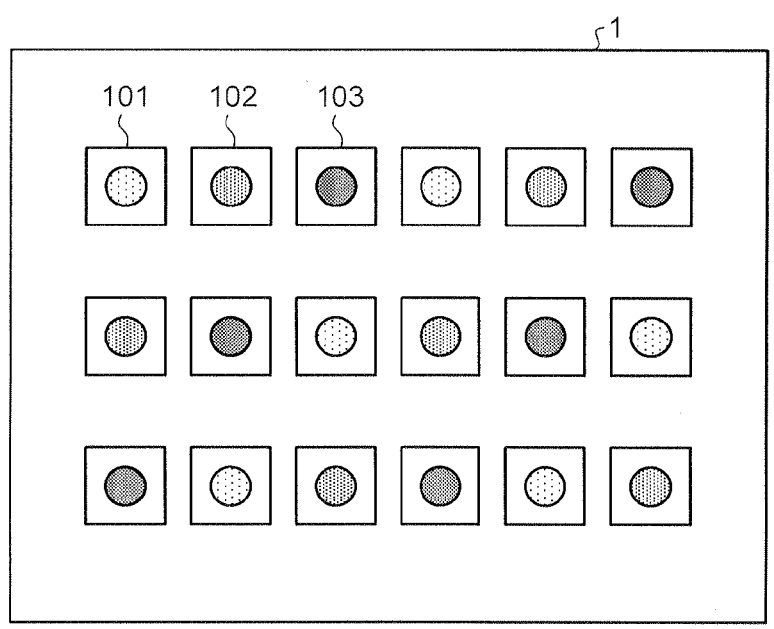
FIG. 2 is a view illustrating an example of an arrangement of light emitters included in a light source.

The light emitters may include LEDs of three or more colors, or may include white LEDs, each having a different color temperature. The light emitters may also include both of them. FIG. 2 is a view illustrating an example of an arrangement of the light emitters included in the light source 1. The light source 1 has a configuration as illustrated in FIG. 2 in which different types of chip LEDs (light emitters 101 to 103) are arranged. In this case, the light emitted from the light source 1 has a mixed color of lights emitted from the respective light emitters. Except for the LED, any other elements can be used as the light emitter, such as a fluorescent tube, a filament lamp, or sodium lamp. The combination of these elements may be used as the light emitter. The light source 1 may further be provided with a light diffuser plate for mixing colors of lights from plural light emitters.

The light source control unit 2 controls the emission of each light emitter constituting the light source 1. Typically, the light source control unit 2 controls the amount of current flowing through each light emitter. The light source control unit 2 may control a voltage applied to each light emitter. A DC current and DC voltage may be controlled, or an AC current and AC voltage may be controlled. Any control method such as PWM control or phase control may be employed. The light source control unit 2 holds therein a table of a value of a spectral distribution of each light emitter in the light source 1. If the number of the types of light emitters is n, this table stores values of each of $P_i(\lambda)$, $(i=1, 2, \ldots, n)$ at a predetermined interval within a region of a visible light. When the emission intensity of each of the light emitters is defined as $a_i(i=1, 2, \ldots n)$, the light source control unit 2 has a function of calculating the spectral power distribution $P(\lambda)$ of the light source 1 according to Equation (2) described below.

$$P(\lambda) = \sum_{i=1}^{n} a_i P_i(\lambda) \quad (2)$$

The light source control unit 2 also has a function of reporting the calculated $P(\lambda)$ to the first calculating unit 4 and the second calculating unit 5. The light source control unit 2 also has a function of receiving estimated values (first evaluation value and second evaluation value) calculated by the first calculating unit 4 and the second calculating unit 5, and determining a vector A by solving an optimization problem having the estimated values defined as target variables.

Figure 3:
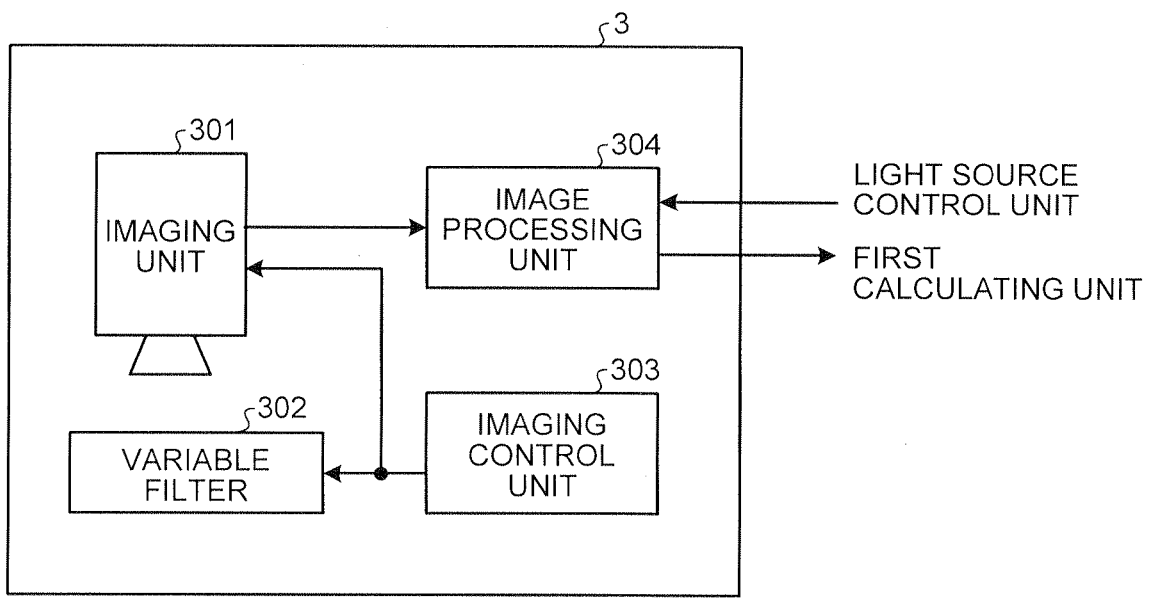
FIG. 3 is a block diagram illustrating an estimation unit according to the first embodiment.

The estimation unit 3 estimates a spectral reflectivity of an object (not illustrated) that is to be illuminated by the illuminating light from the light source 1. FIG. 3 is a block diagram illustrating an example of a configuration of the estimation unit 3 according to the first embodiment. The configuration of the estimation unit 3 will be described below. The estimation unit 3 includes an imaging unit 301, a variable filter 302, an imaging control unit 303, and an image processing unit 304.

The imaging unit 301 is an image sensor such as a CCD camera or a CMOS camera. The spectral sensitivity $S(\lambda)$ of the imaging unit 301 has already been known. The imaging unit 301 images an object, which is illuminated by the illuminating light from the light source 1 through the variable filter 302, in synchronous with the variable filter 302 in accordance with the report from the imaging control unit 303. The captured image is transmitted to the image processing unit 304.

Figure 4:
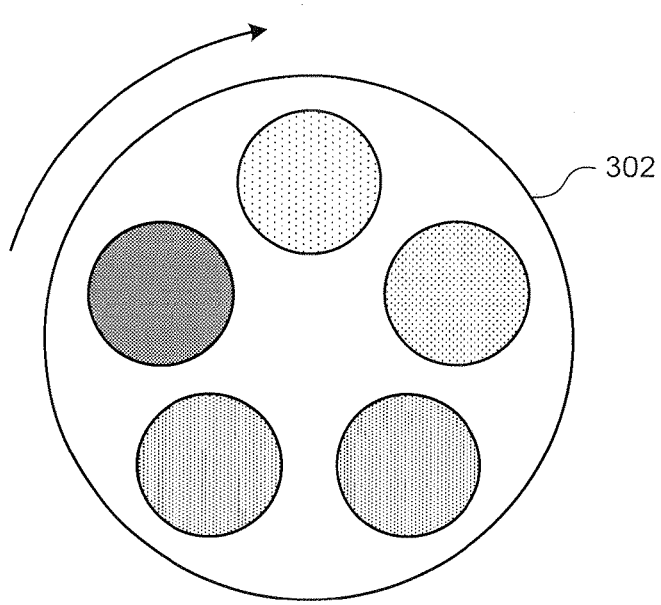
FIG. 4 is a view illustrating an example of a structure of a variable filter.

The variable filter 302 can change plural filters whose spectral transmittance has been known. The variable filter 302 changes the spectral transmittance in accordance with the report from the imaging control unit 303. FIG. 4 is a view illustrating an example of a structure of the variable filter 302. The variable filter 302 is configured such that plural filters, which are physically different, rotate and move so as to change the spectral transmittance of the variable filter 302 as illustrated in FIG. 4. The variable filter 302 may be a liquid crystal tunable filter that can electrically control the spectral transmittance. Supposing that m types of spectral transmittances can be realized, each spectral transmittance is defined as $T_j(\lambda)$, $(j=1, 2, \ldots, m)$.

The imaging control unit 303 controls the variable filter 302 and the imaging unit 301 such that the variable filter 302 changes the spectral transmittance, and then, the imaging unit 301 captures an image.

The image processing unit 304 estimates the spectral reflectivity of the object, which is illuminated by the illuminating light from the light source 1, from plural images captured by the imaging unit 301 under different spectral transmittances of the variable filter 302. The method of estimating the spectral reflectivity by the image processing unit 304 is as described below.

The spectral reflectivity on any portion of the object is defined as $R(\lambda)$, the spectral power distribution of the light source 1 is defined as $P(\lambda)$, the spectral sensitivity of the imaging unit 301 is defined as $S(\lambda)$, and the spectral transmittance that can be changed by the variable filter 302 is defined as $T_j(\lambda)$, $(j=1, 2, \ldots, m)$. The values of $S(\lambda)$ and $T_j(\lambda)$ are held as a table (not illustrated) in the image processing unit 304, for example.

The output value $V_j$ of the imaging unit 301 to the object, captured through the variable filter 302 whose spectral transmittance is changed to the jth spectral transmittance, is represented by Equation (3) described below.

$$V_j = \int_{\lambda_1}^{\lambda_w} P(\lambda) R(\lambda) T_j(\lambda) S(\lambda) d\lambda \quad (3)$$

$\lambda_1$ and $\lambda_w$ respectively indicate a lower limit and an upper limit of a wavelength where the sensitivity of the imaging unit 301 is guaranteed. When the integration described above is approximated by a discrete value, and resolved, a determinant illustrated by Equation (4) is obtained. Here, $\Delta\lambda$ is a quantization range for performing the discretization.

$$\begin{bmatrix} V_1 \\ V_2 \\ \vdots \\ V_m \end{bmatrix} = \quad (4)$$

$$\begin{bmatrix} P(\lambda_1)T_1(\lambda_1)S(\lambda_1)\Delta\lambda & P(\lambda_2)T_1(\lambda_2)S(\lambda_2)\Delta\lambda & \cdots & P(\lambda_w)T_1(\lambda_w)S(\lambda_w)\Delta\lambda \\ P(\lambda_1)T_2(\lambda_1)S(\lambda_1)\Delta\lambda & P(\lambda_2)T_2(\lambda_2)S(\lambda_2)\Delta\lambda & \cdots & P(\lambda_w)T_2(\lambda_w)S(\lambda_w)\Delta\lambda \\ \vdots & \vdots & \vdots & \vdots \\ P(\lambda_1)T_m(\lambda_1)S(\lambda_1)\Delta\lambda & P(\lambda_2)T_m(\lambda_2)S(\lambda_2)\Delta\lambda & \cdots & P(\lambda_w)T_m(\lambda_w)S(\lambda_w)\Delta\lambda \end{bmatrix} \begin{bmatrix} R(\lambda_1) \\ R(\lambda_2) \\ \vdots \\ R(\lambda_w) \end{bmatrix}$$

When the matrix at the left in the right side in Equation (4) is put as F, and a pseudo inverse matrix G of F is obtained by wiener method, the spectral reflectivity $R(\lambda)$ of the object can be obtained by Equation (5) described below.

$$\begin{bmatrix} R(\lambda_1) \\ R(\lambda_2) \\ \vdots \\ R(\lambda_w) \end{bmatrix} = G \begin{bmatrix} V_1 \\ V_2 \\ \vdots \\ V_m \end{bmatrix} \quad (5)$$

In the above description, the number of channels of the imaging unit 301 is 1 (the monochromatic image). If the imaging unit 301 having 3 channels of REB is used, for example, the number of the equations in Equation (4) can be tripled. Therefore, the spectral reflectivity can be estimated with high precision.

The method of estimating the spectral reflectivity of the object is not limited thereto. Any other techniques may be used.

The second calculating unit 5 estimates a non-visual influence quantity Y1 of the illumination based on the spectral power distribution $P(\lambda)$ of the light source 1 reported from the light source control unit 2. The estimated non-visual influence quantity Y1 is reported to the light source control unit 2.

The non-visual influence quantity Y1 (second evaluation value) indicates how much the influence is given by the illuminating light to non-visual factors. For example, the non-visual influence quantity Y1 is a value of integral of a product of a action spectrum for melatonin suppression and the spectral power distribution $P(\lambda)$ of the light source 1. The value of the melatonin secretory inhibition prediction expression considering a response of a cone, a rod, and a melanopsin-containing ganglion cell into may be employed as the non-visual influence quantity Y1.

The value of integral of the product of the melatonin secretory inhibiting action spectral and the spectral power distribution of the light source 1 is defined by Equation (6) described below wherein the spectral power distribution of the light source 1 is defined as $P(\lambda)$, and the action spectrum for melatonin suppression is defined as $M_1(\lambda)$.

$$Y_1 = \int_{380\,nm}^{730\,nm} P(\lambda) M_1(\lambda) d\lambda \quad (6)$$

The value of the melatonin secretory inhibition prediction expression considering the response of a cone, a rod, and a melanopsin-containing ganglion cell is classified according to a value of T (Equation (7)). When T≥0, it can be calculated by Equation (8), and when T<0, it can be calculated by Equation (9).

$$T = \int_{380\,nm}^{730\,nm} P(\lambda) S(\lambda) d\lambda - k \int_{380\,nm}^{730\,nm} P(\lambda) V_{10}(\lambda) d\lambda \quad (7)$$

$$Y_1 = \left[ \left( \alpha_1 \int_{380\,nm}^{730\,nm} P(\lambda) M_2(\lambda) d\lambda - b_1 \right) + \right. \quad (8)$$
$$\alpha_2 \left( \int_{380\,nm}^{780\,nm} P(\lambda) S(\lambda) d\lambda - k \int_{380\,nm}^{730\,nm} P(\lambda) V_{10}(\lambda) d\lambda \right) - b_2 \right] -$$
$$\alpha_3 \left[ 1 - \exp\left( -\frac{\int_{380\,nm}^{730\,nm} P(\lambda) V'(\lambda) d\lambda}{rodSat} \right) \right]$$

$$Y_1 = \alpha_1 \int_{380\,nm}^{730\,nm} P(\lambda) M_2(\lambda) d\lambda - b_1 \quad (9)$$

Here, constants are set as k=0.31, $\alpha_1$=0.285, $\alpha_2$=0.2, $\alpha_3$=0.72, b1=0.01, b2=0.001, and rodsat=6.5. $M_2(\lambda)$ is the spectral reaction sensitivity of the melanopsin-containing ganglion cell, $V_{10}(\lambda)$ is the spectral reaction sensitivity of an L cone and M cone, $V'(\lambda)$ is the spectral reaction sensitivity of the rod, and $S(\lambda)$ is the spectral sensitivity of an S cone.

The first calculating unit 4 calculates the output value (first evaluation value) indicating an adequacy of a color of an object (color appearance of an object) visually perceived, based on the spectral distribution of the light source 1 and the spectral reflectivity of the object. For example, the first calculating unit 4 estimates the color appearance of the object under a standard light source based on the value $R(\lambda)$, estimated by the estimation unit 3, of the spectral reflectivity of the object illuminated by the illuminating light from the light source 1, and the value $P(\lambda)$ of the spectral power distribution of the light source 1 determined by the light source control unit 2. The specific method of the estimation will be described below.

Firstly, the first calculating unit 4 obtains a correlated color temperature of emission color by the spectral power distribution $P(\lambda)$ of the light source 1, and determines the light source used as the standard light source. When the correlated color temperature of $P(\lambda)$ is less than 5000 K, the first calculating unit 4 defines light with the correlated color temperature equal to $P(\lambda)$ of a complete radiator as the standard light source. When it is 5000 K or more, the first calculating unit 4 defines light with the correlated color temperature equal to $P(\lambda)$ of CIE daylight as the standard light source. The value of the spectral distribution of the standard light source obtained here is defined as $S(\lambda)$ below. This value is stored as a table (not illustrated) in the first calculating unit 4, for example.

A coordinate value $(X_p, Y_p, Z_p)$ corresponding to the light source 1 in an XYZ color system and a coordinate value $(X_s, Y_s, Z_s)$ corresponding to the standard light source are obtained by Equation (10) to Equation (17) described below.

$$X_p = K_p \int_{380\,nm}^{780\,nm} P(\lambda) \bar{x}(\lambda) d\lambda \quad (10)$$

$$Y_p = K_p \int_{380\,nm}^{780\,nm} P(\lambda) \bar{y}(\lambda) d\lambda \quad (11)$$

$$Z_p = K_p \int_{380\,nm}^{780\,nm} P(\lambda) \bar{z}(\lambda) d\lambda \quad (12)$$

wherein $$K_p = \frac{100}{\int_{380\,nm}^{780\,nm} P(\lambda)\dot{y}(\lambda)\,d\lambda} \quad (13)$$

$$X_s = K_s \int_{380\,nm}^{780\,nm} S(\lambda)\dot{x}(\lambda)\,d\lambda \quad (14)$$

$$Y_s = K_s \int_{380\,nm}^{780\,nm} S(\lambda)\dot{y}(\lambda)\,d\lambda \quad (15)$$

$$Z_s = K_s \int_{380\,nm}^{780\,nm} S(\lambda)\dot{z}(\lambda)\,d\lambda \quad (16)$$

wherein $$K_s = \frac{100}{\int_{380\,nm}^{780\,nm} S(\lambda)\dot{y}(\lambda)\,d\lambda} \quad (17)$$

wherein $\dot{x}(\lambda)$, $\dot{y}(\lambda)$, $\dot{z}(\lambda)$ are color-matching functions in an XYZ color system.

Next, a coordinate value $(u_p, v_p)$ corresponding to the light source 1 on a CIE1960UCS chromaticity diagram and a coordinate value $(u_s, v_s)$ corresponding to the standard light source are obtained by Equation (18) to Equation (21) described below.

$$u_s = \frac{4X_s}{X_s + 15Y_s + 3Z_s} \quad (18)$$

$$v_s = \frac{6Y_s}{X_s + 15Y_s + 3Z_s} \quad (19)$$

$$u_p = \frac{4X_p}{X_p + 15Y_p + 3Z_p} \quad (20)$$

$$v_p = \frac{6Y_p}{X_p + 15Y_p + 3Z_p} \quad (21)$$

A value $(X_{pr}, Y_{pr}, Z_{pr})$ of a tristimulus value of an object color under the light source 1 and a value $(X_{sr}, Y_{sr}, Z_{sr})$ thereof under the standard light source are obtained by Equation (22) to Equation (29) described below.

$$X_{sr} = K_p \int_{380\,nm}^{780\,nm} S(\lambda)R(\lambda)\dot{x}(\lambda)\,d\lambda \quad (22)$$

$$Y_{sr} = K_p \int_{380\,nm}^{780\,nm} S(\lambda)R(\lambda)\dot{y}(\lambda)\,d\lambda \quad (23)$$

$$Z_{sr} = K_p \int_{380\,nm}^{780\,nm} S(\lambda)R(\lambda)\dot{z}(\lambda)\,d\lambda \quad (24)$$

wherein $$K_{sr} = \frac{100}{\int_{380\,nm}^{780\,nm} S(\lambda)R(\lambda)\dot{y}(\lambda)\,d\lambda} \quad (25)$$

$$X_{pr} = K_p \int_{380\,nm}^{780\,nm} P(\lambda)R(\lambda)\dot{x}(\lambda)\,d\lambda \quad (26)$$

$$Y_{pr} = K_p \int_{380\,nm}^{780\,nm} P(\lambda)R(\lambda)\dot{y}(\lambda)\,d\lambda \quad (27)$$

$$Z_{pr} = K_p \int_{380\,nm}^{780\,nm} P(\lambda)R(\lambda)\dot{z}(\lambda)\,d\lambda \quad (28)$$

wherein $$K_{pr} = \frac{100}{\int_{380\,nm}^{780\,nm} P(\lambda)R(\lambda)\dot{y}(\lambda)\,d\lambda} \quad (29)$$

From these values, a coordinate value $(u_{pr}, v_{pr})$ under the light source 1 on the CIE1960UCS chromaticity diagram and a coordinate value $(u_{sr}, v_{sr})$ under the standard light source are obtained by Equation (30) to Equation (33) described below.

$$u_{sr} = \frac{4X_{sr}}{X_{sr} + 15Y_{sr} + 3Z_{sr}} \quad (30)$$

$$v_{sr} = \frac{6Y_{sr}}{X_{sr} + 15Y_{sr} + 3Z_{sr}} \quad (31)$$

$$u_{pr} = \frac{4X_{pr}}{X_{pr} + 15Y_{pr} + 3Z_{pr}} \quad (32)$$

$$v_{pr} = \frac{6Y_{pr}}{X_{pr} + 15Y_{pr} + 3Z_{pr}} \quad (33)$$

Next, a chromatic-adaptation transform is executed in accordance with Equation (34) to Equation (37) described below.

$$u'_p = u_s \quad (34)$$

$$v'_p = v_s \quad (35)$$

$$u'_{pr} = \frac{10.872 + 0.404\frac{c_s}{c_p}c_{pr} - 4\frac{d_s}{d_p}d_{pr}}{16.518 + 1.481\frac{c_s}{c_p}c_{pr} - 4\frac{d_s}{d_p}d_{pr}} \quad (36)$$

$$v'_{pr} = \frac{5.520}{16.518 + 1.481\frac{c_s}{c_p}c_{pr} - 4\frac{d_s}{d_p}d_{pr}} \quad (37)$$

Here, $c_s$, $c_p$, $c_{pr}$, $d_s$, $d_p$, and $d_{pr}$ are obtained by Equation (38) to Equation (43) described below.

$$c_s = \frac{1}{v_s}(4.0 - u_s - 10.0v_s) \quad (38)$$

$$c_p = \frac{1}{v_p}(4.0 - u_p - 10.0v_p) \quad (39)$$

$$c_{pr} = \frac{1}{v_{pr}}(4.0 - u_{pr} - 10.0v_{pr}) \quad (40)$$

$$v_s = \frac{1}{v_s}(1.708v_s + 0.404 - 1.481u_s) \quad (41)$$

$$v_p = \frac{1}{v_p}(1.708v_p + 0.404 - 1.481u_p) \quad (42)$$

$$v_{pr} = \frac{1}{v_{pr}}(1.708v_{pr} + 0.404 - 1.481u_{pr}) \quad (43)$$

A coordinate $(W^*_{sr}, U^*_{sr}, V^*_{sr})$ under the standard light source in a CIE1964 uniform color space and a coordinate $(W^*_{pr}, U^*_{pr}, V^*_{pr})$ under the light source 1 are obtained by Equation (44) to Equation (49) described below.

$$W^*_{sr} = 25(Y_{sr})^{1/3} - 17 \quad (44)$$

$$U^*_{sr} = 13W^*_{sr}(u_{sr} - u_s) \quad (45)$$

$$V^*_{sr}=13W^*_{sr}(v_{sr}-u_s) \quad (46)$$

$$W^*_{pr}=25(Y_{pr})^{1/3}-17 \quad (47)$$

$$U^*_{pr}=13W^*_{pr}(u'_{pr}-u'_p) \quad (48)$$

$$V^*_{pr}=13W^*_{pr}(v'_{pr}-v'_p) \quad (49)$$

A chromaticity difference ΔE is obtained by Equation (50) described below through the procedure described above.

$$\Delta E=\sqrt{(W^*_{sr}-W^*_{pr})^2+(U^*_{sr}-U^*_{pr})^2+(V^*_{sr}-V^*_{pr})^2} \quad (50)$$

The value of ΔE is obtained for each pixel of the image captured by the imaging unit 301. Therefore, the value of each pixel is defined as $\Delta E_{hw}$(h=1, 2, ..., H)(w=1, 2, ..., W), and the total of the chromaticity difference of the whole image is specified as farness in color appearance under two illuminations.

$$\Delta E_{sum} = \sum_{h=1}^{H} \sum_{w=1}^{W} \Delta E_{hw} \quad (51)$$

In Equation (51), the values are summed up over the whole region of the image. However, only the values in a specific region may be considered into.

A closeness in the color appearance can be defined by any function Y2=F($\Delta E_{sum}$), wherein Y2 becomes smaller as the value of $\Delta E_{sum}$ increases. The value Y2 of the closeness in the color appearance becomes the output value (first evaluation value) of the first calculating unit 4.

The method described above is a method of calculating the color appearance under the standard light source in the CIE1964 uniform color space and the closeness in the color appearance under the light source 1 of the illuminating device 100. This method can be replaced by a method of obtaining a chromaticity difference in another color space such as L*a*b* color space. Alternatively, an equation of chromaticity difference such as CIEDE2000 can be used instead.

Figure 5:
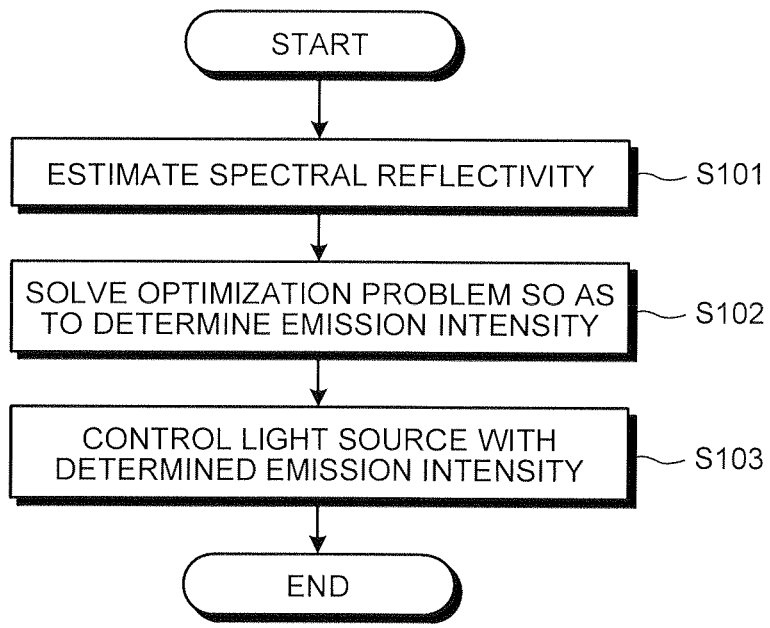
FIG. 5 is a flowchart illustrating a control process according to the first embodiment.

The control process of the illuminating device 100 thus configured according to the first embodiment will be described next with reference to FIG. 5. FIG. 5 is a flowchart illustrating the whole control process according to the first embodiment.

The estimation unit 3 estimates the spectral reflectivity of an object illuminated by the illumination (step S101), The result of the estimation is reported to the first calculating unit 4.

The light source control unit 2 optimizes the vector A (A=$a_1 a_2 a_3 ... a_n$), which is a value determining the emission intensity of the light source 1, based on the optimization condition determined beforehand (step S102). In this case, the light source control unit 2 reports a value of P(λ) corresponding to a temporary vector A to the second calculating unit 5 and the first calculating unit 4. The second calculating unit 5 and the first calculating unit 4 return the estimated values Y1 and Y2 corresponding to the value of the temporary vector A. The condition for optimization used here is the one for minimizing Y1 with Y2 being kept to be not less than a certain value. This is mathematically a general optimization problem with restraint condition. The value of the vector A satisfying the above-mentioned condition can be obtained by using a general optimization method such as a gradient method or simulated annealing.

The light source control unit 2 controls such that each of the light emitters of the light source 1 emits light based on the determined value of the vector A (step S103).

With this process, when an object that hardly reflects blue light (especially, light with a wavelength near 460 nm) is illuminated, for example, the light source 1 does not have to contain blue light even if the value of Y2 is likely to be kept large. On the other hand, if the value of the color rendering index is likely to be kept large as in the related case, the light source 1 has to contain blue light. Therefore, the present embodiment that tries to keep the value of Y2 large can reduce the value of Y1 more than the related method that tries to keep the value of the color rendering index. Specifically, the present embodiment can efficiently reduce the non-visual influence due to the illumination without deteriorating the color appearance of an object illuminated by the illumination.

The restraint condition used in step S102 is not limited to the condition in which the Y1 is minimized with the Y2 being kept to be not less than a certain value. For example, the condition such that the Y2 is maximized with the Y1 being kept to be not more than a certain value may be employed, if the reduction in the non-visual influence takes priority. If an arousal level is to be enhanced, the condition such that the Y1 is maximized with the Y2 being kept to be not less than a certain value may be employed.

Modification of First Embodiment

Figure 6:
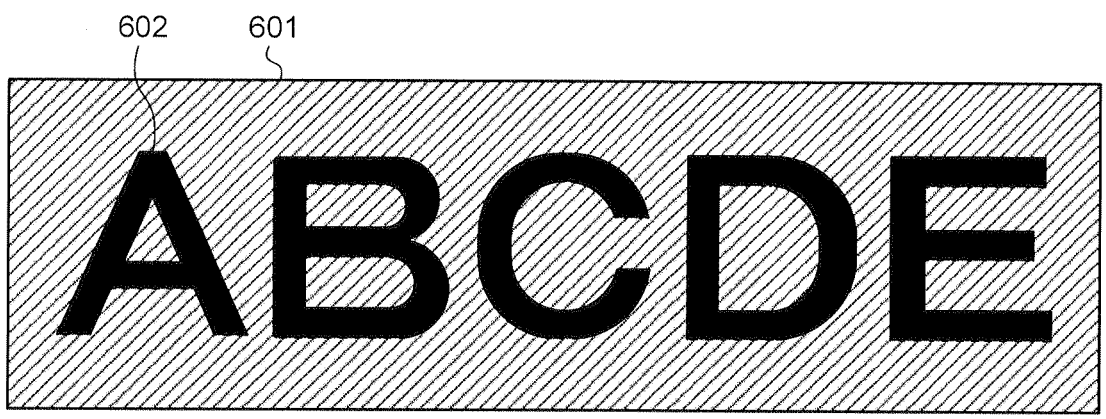
FIG. 6 is a view illustrating one example of an object illuminated by illuminating light containing plural colors.

FIG. 6 is a view illustrating one example of an object illuminated by illuminating light containing plural colors. As illustrated in FIG. 6, characters 602 having a spectral reflectivity of $R_B(\lambda)$ are written on a background 601 having a spectral reflectivity of $R_A(\lambda)$. If the chromaticity difference of the colors perceived in the region of the background 601 and the region of the characters 602 is sufficiently great, the characters 602 can be read even if the colors are greatly shifted from the colors perceived under the standard light source.

Specifically, the value of Y2 used for obtaining the vector A by solving the above-mentioned optimization problem may be replaced by a chromaticity difference in plural regions, each having different spectral reflectivity. For this replacement, what is done in the first calculating unit 4 is replaced as described below in the present modification.

Firstly, a cluster analysis is performed to the value R(λ) of the spectral reflectivity of each pixel estimated by the estimation unit 3. With this process, the value R(λ) of the spectral reflectivity is classified into a cluster belonging to each region. The values of the spectral reflectivity corresponding to the representative values (e.g., centroids) of the first region and the second region are set as $R_1(\lambda)$ and $R_2(\lambda)$.

The coordinate in the CIE1964 uniform color space under the light source 1 can be calculated in the same manner as in the above-mentioned method. The coordinate of the first region is set as ($W^*_{pr1}$, $U^*_{pr1}$, $V^*_{pr1}$), and the coordinate of the second region is set as ($W^*_{pr2}$, $U^*_{pr2}$, $V^*_{pr2}$).

The chromaticity difference ΔE12 between the first region and the second region can be obtained by Equation (52) described below. This value can be set as the output value Y2 of the first calculating unit 4.

$$\Delta E_{12}=\sqrt{(W^*_{pr1}-W^*_{pr2})^2+(U^*_{pr1}-U^*_{pr2})^2+(V^*_{pr1}-V^*_{pr2})^2} \quad (52)$$

In this modification, the method of obtaining the chromaticity difference in the CIE1964 uniform color space can be replaced by a method of obtaining a chromaticity difference in another color space such as L*a*b* color space. Alternatively, an equation of chromaticity difference such as CIEDE2000 can be used instead.

The above-mentioned process is for the case in which there are two regions, each having a different spectral reflectivity. However, the similar process can be applied to the case in which there are three or more regions. In this case, the chromaticity difference may be calculated for each combination of the respective regions, and its average or minimum value may be set as the output value of the first calculating unit 4.

For example, when characters (reflecting generally wavelengths of red, green and blue) that look white under the white light source are written on a background (that hardly reflects light of all wavelengths) that looks black under the white light source, the characters look yellow, which is very far from black, even if the light source 1 does not contain blue light, because the character region reflects light having wavelengths of red and green. Therefore, the value of Y2 can be kept large without the inclusion of the blue light that gives a great non-visual influence. Specifically, the present modification can more efficiently reduce the non-visual influence.

The case between the background color and the character color is described above. However, the modification is applicable for a case except for the case between the background and characters, e.g., for a case in which different colors can be distinguished (e.g., check for defective goods).

Second Embodiment

Figure 7:
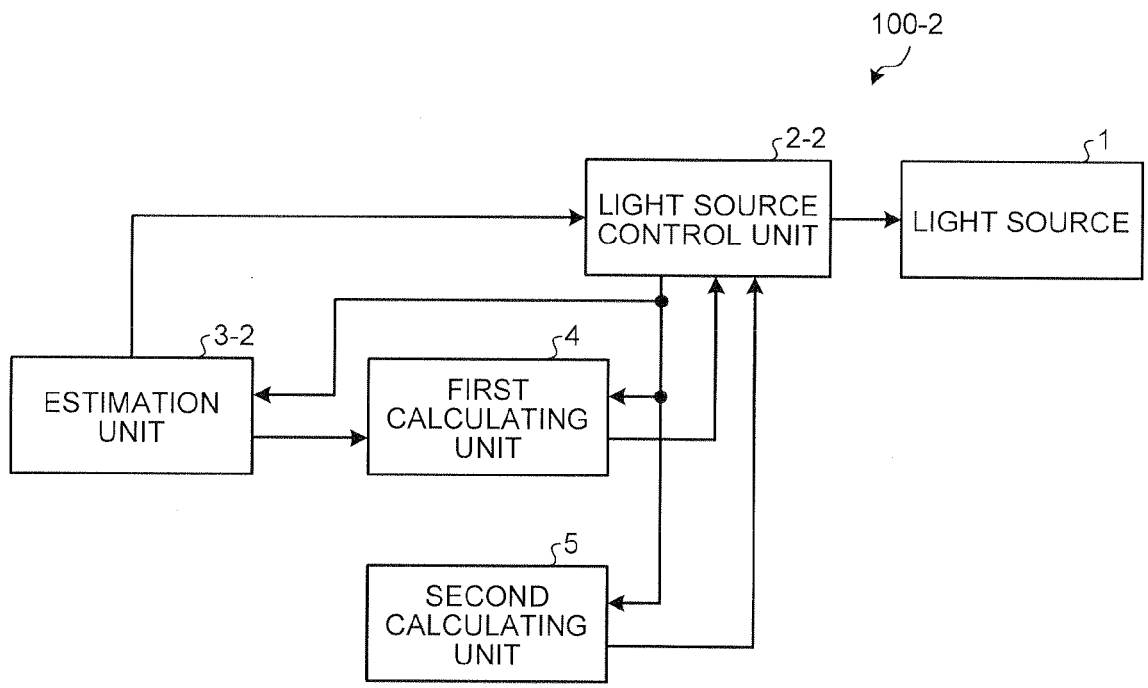
FIG. 7 is a block diagram illustrating an illuminating device according to a second embodiment.

FIG. 7 is a block diagram illustrating an example of a configuration of an illuminating device 100-2 according to a second embodiment. As illustrated in FIG. 7, the illuminating device 100-2 includes a light source 1, a light source control unit 2-2, an estimation unit 3-2, a first calculating unit 4, and a second calculating unit 5.

In the second embodiment, the functions of the light source control unit 2-2 and the estimation unit 3-2 are different from those in the first embodiment. The other components and functions are similar to those in FIG. 1, which is the block diagram of the illuminating device 100 according to the first embodiment. Therefore, the same components are identified by the same numerals, and redundant description thereof will not be repeated here.

Instead of the function of the light source control unit 2 in the first embodiment, the light source control unit 2-2 has a function of controlling the spectral distribution of the light source 1 in accordance with the input from the estimation unit 3-2.

Figure 8:
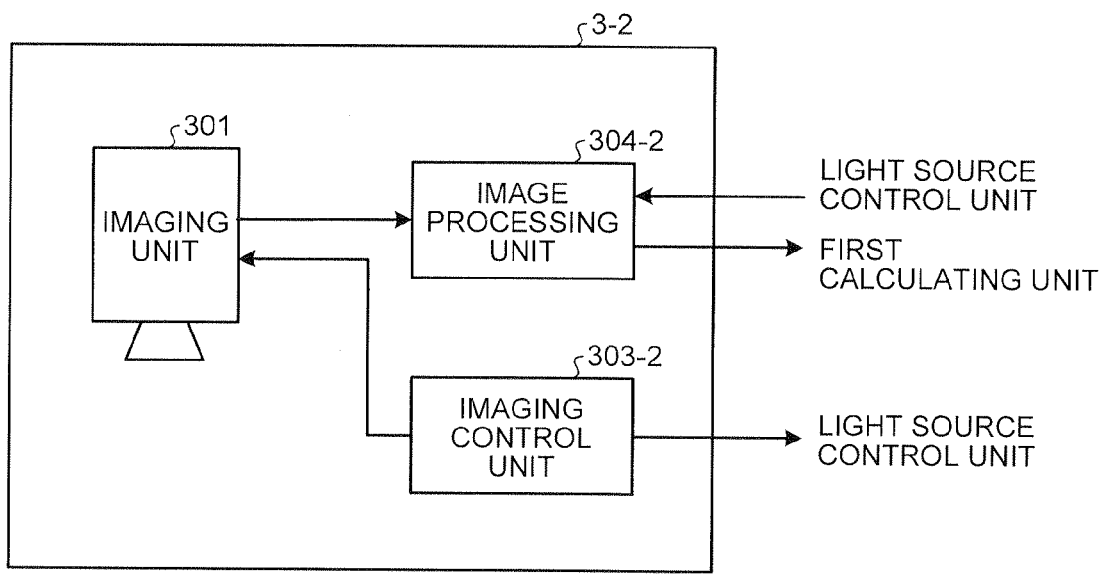
FIG. 8 is a block diagram illustrating an estimation unit according to the second embodiment.

The estimation unit 3-2 has a function of estimating the spectral reflectivity of an object illuminated by the illuminating light from the light source 1, and also has a function of giving an instruction to the light source control unit 2-2 to change the spectral distribution. FIG. 8 is a block diagram illustrating the estimation unit 3-2 according to the second embodiment. The estimation unit 3-2 includes an imaging unit 301, an imaging control unit 303-2, and an image processing unit 304-2. The estimation unit 3-2 in the second embodiment is different from that in the first embodiment in that it does not include the variable filter 302.

The imaging control unit 303-2 issues a request of changing the spectral distribution of the light source 1 and a request of sequentially executing an image-capture by the imaging unit 301 to the light source control unit 2-2. The light source control unit 2-2 controls the light source 1 to have different m types of spectral distributions according to the request.

The image processing unit 304-2 estimates the spectral reflectivity of the object, which is illuminated by the illuminating light from the light source 1, from plural images captured by the imaging unit 301 under different spectral distributions of the light source 1. The method of estimating the spectral reflectivity by the image processing unit 304-2 according to the present embodiment is as described below.

The spectral reflectivity on any portion of the object is defined as $R(\lambda)$, the m types of spectral distributions of the light source 1 are defined as $P_j(\lambda)$, (j=1, 2, . . . , m), and the spectral sensitivity of the imaging unit 301 is defined as $S(\lambda)$.

The output value $V_j$ of the imaging unit 301 to the object captured under the light source 1 having the j-th type of spectral distribution is represented by Equation (53) described below.

$$V_j = \int_{\lambda_1}^{\lambda_w} P_j(\lambda) R(\lambda) S(\lambda) d\lambda \quad (53)$$

When the integration described above is approximated by a discrete value, and resolved, a determinant illustrated by Equation (54) is obtained.

$$\begin{bmatrix} V_1 \\ V_2 \\ \vdots \\ V_m \end{bmatrix} = \begin{bmatrix} P_1(\lambda_1)S(\lambda_1)\Delta\lambda & P_1(\lambda_2)S(\lambda_2)\Delta\lambda & \ldots & P_1(\lambda_w)S(\lambda_w)\Delta\lambda \\ P_2(\lambda_1)S(\lambda_1)\Delta\lambda & P_2(\lambda_2)S(\lambda_2)\Delta\lambda & \ldots & P_2(\lambda_w)S(\lambda_w)\Delta\lambda \\ \vdots & \vdots & \vdots & \vdots \\ P_m(\lambda_1)S(\lambda_1)\Delta\lambda & P_m(\lambda_2)S(\lambda_2)\Delta\lambda & \ldots & P_m(\lambda_w)S(\lambda_w)\Delta\lambda \end{bmatrix} \begin{bmatrix} R(\lambda_1) \\ R(\lambda_2) \\ \vdots \\ R(\lambda_w) \end{bmatrix} \quad (54)$$

When the matrix at the left in the right side in Equation (54) is put as F, and a pseudo inverse matrix G of F is obtained by wiener method, the spectral reflectivity $R(\lambda)$ of the object can be obtained by Equation (55) described below.

$$\begin{bmatrix} R(\lambda_1) \\ R(\lambda_2) \\ \vdots \\ R(\lambda_w) \end{bmatrix} = G \begin{bmatrix} V_1 \\ V_2 \\ \vdots \\ V_m \end{bmatrix} \quad (55)$$

As in the first embodiment, if the imaging unit 301 having 3 channels of RGB is used, for example, the number of the equations in Equation (54) can be tripled. Therefore, the spectral reflectivity can be estimated with high precision.

As described above, even the illuminating device according to the second embodiment that does not include the variable filter can provide the same effect as that of the first embodiment. The variable filter can further be provided in the second embodiment, as in the first embodiment. In this case, when the types of the variable filter are defined as $m_1$, and the types of the different spectral distributions by the light source 1 are defined as $m_2$, the number of the equations in Equation (54) can be a maximum of $m_1 \times m_2$. Accordingly, the spectral reflectivity of the object can more precisely be estimated.

Third Embodiment

Figure 9:
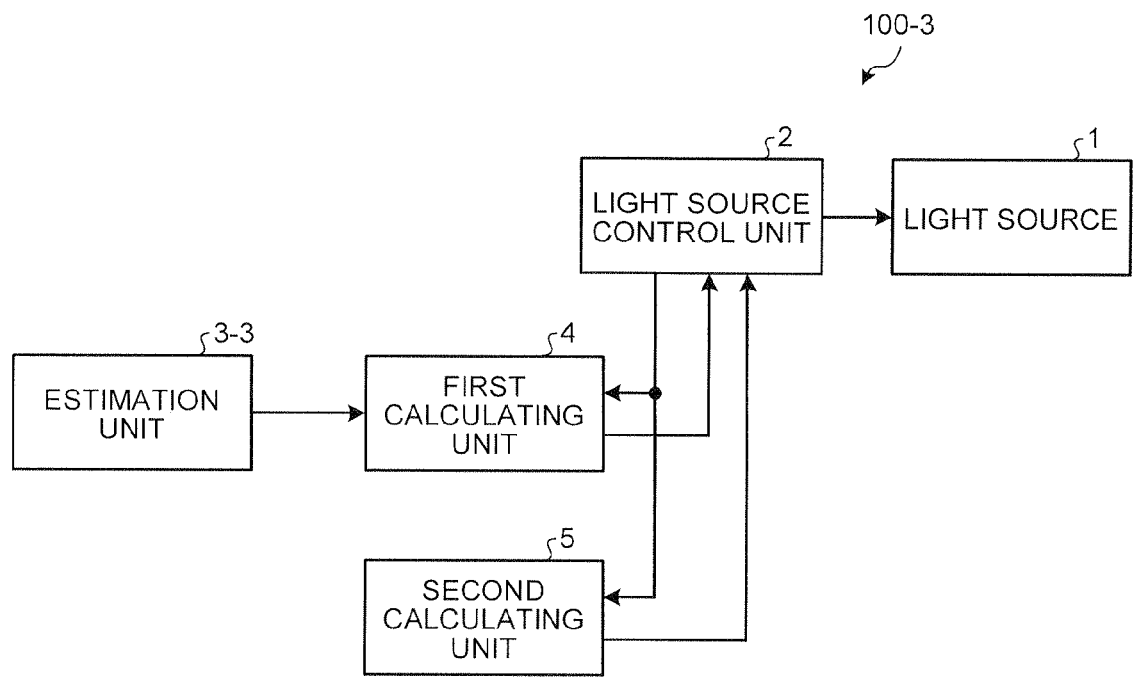
FIG. 9 is a block diagram illustrating an illuminating device according to a third embodiment.

In the third embodiment, spectral reflectivity of an object illuminated by an illuminating device is estimated based on a user's manual input. FIG. 9 is a block diagram illustrating an example of a configuration of an illuminating device 100-3 according to the third embodiment. As illustrated in FIG. 9, the illuminating device 100-3 includes a light source 1, a light source control unit 2, an estimation unit 3-3, a first calculating unit 4, and a second calculating unit 5.

Figure 10:
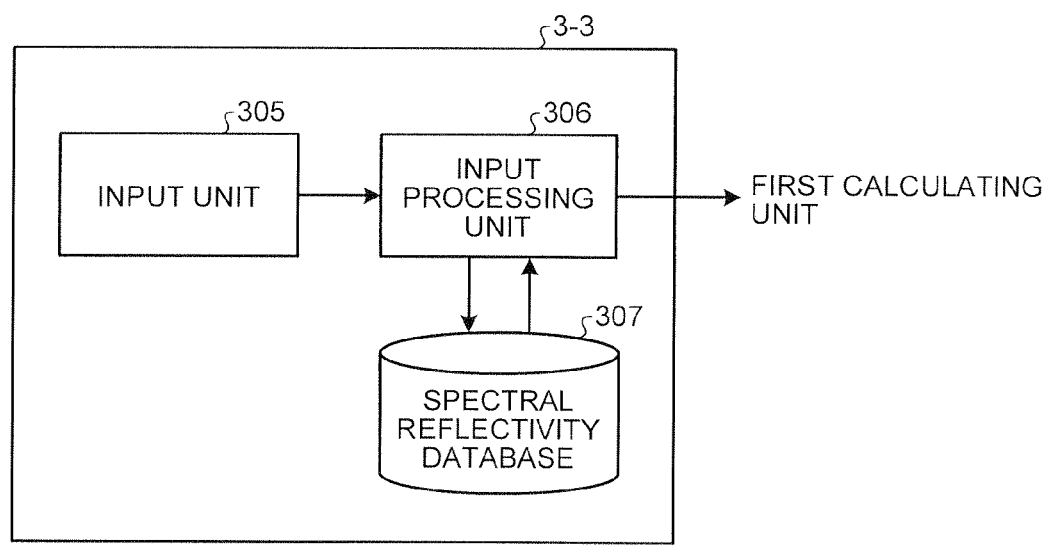
FIG. 10 is a block diagram illustrating an estimation unit according to the third embodiment.

FIG. 10 is a block diagram illustrating an example of a configuration of the estimation unit 3-3 according to the third embodiment. The estimation unit 3-3 includes an input unit 305, an input processing unit 306, and a spectral reflectivity database 307.

Figure 11:
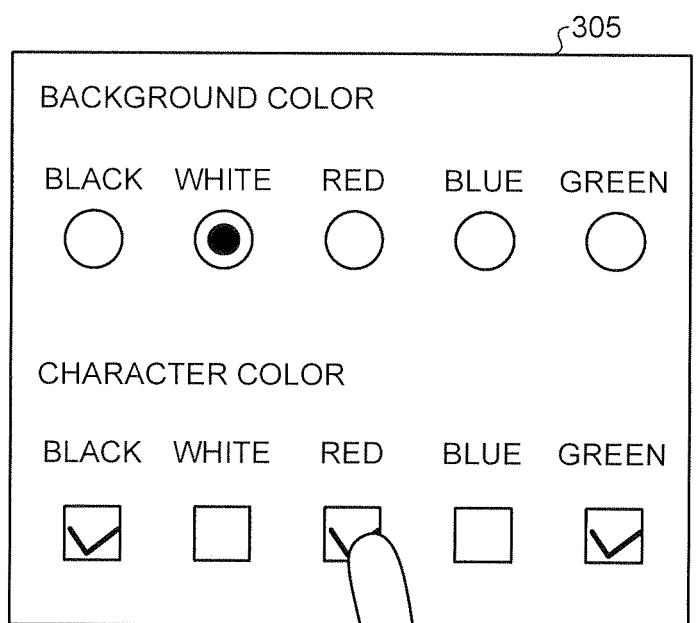
FIG. 11 is a view illustrating an example of a configuration of an input unit.

The input unit 305 is composed of a touch panel display, for example. FIG. 11 is a view illustrating an example of a configuration of the input unit 305. As illustrated in FIG. 11, the user uses the input unit 305 to select a color used for an object (e.g., a book) illuminated by the illumination. The information selected in the input unit 305 is reported to the input processing unit 306. The input unit 305 may be composed of a physical button or the like, instead of the touch panel display.

The input processing unit 306 estimates a spectral reflectivity with reference to the spectral reflectivity database 307 based on the information reported from the input unit 305. The result of the estimation is reported to the first calculating unit 4.

The spectral reflectivity database 307 is a storage unit that stores spectral reflectivity of a typical (average) sheet or ink for each color, for example. The spectral reflectivity database 307 can be composed of a storage medium popularly used, such as HDD (Hard Disk Drive), an optical disk, a memory card, and a RAM (Random Access Memory).

The spectral reflectivity database 307 transmits the value of the spectral reflectivity P(λ) corresponding to each color to the input processing unit 306 in accordance with the inquiry from the input processing unit 306. The spectral reflectivity database 307 may be present on external network such as Web. In this case, the input processing unit 306 has a function of connecting to the network.

With this configuration, the estimation unit 3-3 in the third embodiment can estimate the spectral reflectivity of the object. The third embodiment can realize functions like those of the first and second embodiments without mounting a high-cost camera (imaging unit) or variable filter to the estimation unit 3-3.

Modification of Third Embodiment

In the present modification, a user does not directly designate a color of an object illuminated by the illumination, but designates a name of an object illuminated by the illumination.

Figure 12:
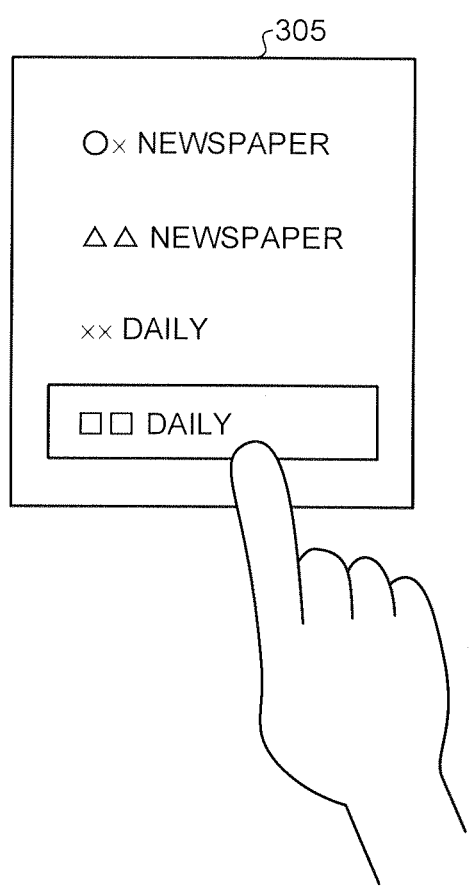
FIG. 12 is a view illustrating an example of a modification of an input unit.

FIG. 12 is a view illustrating an example of a configuration of the input unit 305 in the present modification. In the present modification, the user can select a proper name or popular name of an object illuminated by the illumination, as illustrated in FIG. 12. A manner other than that of designating a specific publication as illustrated in FIG. 12 may be employed. For example, it can be configured such that the object is designated in a rough classification such as "newspaper", "weekly pictorial magazine", or "paperback book". The object that can be selected is not limited to the above-mentioned publications.

The spectral reflectivity database 307 stores spectral reflectivity for the sheet and each color of ink used for the object designated by the input unit 305. The spectral reflectivity database 307 transmits the spectral reflectivity P(λ) corresponding to each of the used colors to the input processing unit 306 in accordance with the inquiry from the input processing unit 306. The spectral reflectivity database 307 may be provided or may be present on external network such as Web. The spectral reflectivity database 307 can be configured such that, when a new magazine is first published, or when a used sheet or a type of used ink is changed, the content thereof can be updated on a case-by-case basis.

The present modification can spare the user the trouble of designating the color of the object illuminated by the illumination. Since the spectral reflectivity of the actual object can be used, the spectral distribution of the light source can be optimized based on the highly-precise spectral reflectivity.

As described above, the first to the third embodiments can evaluate a color appearance of an object, which is illuminated by illuminating light from the light source, in consideration of the spectral reflectivity of the object, in order to prevent light with a wavelength unnecessary for keeping the color appearance of the object from being contained in the illuminating light. Consequently, the non-visual influence can more efficiently be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An illuminating device comprising:
a light source configured to include plural light emitters, each having a different spectral distribution;
a light source control unit configured to determine an emission intensity of each of the light emitters, and control the light emitters to have the emission intensities;
an estimation unit configured to estimate a spectral reflectivity of an object to which illuminating light is irradiated from the light source;
a first calculating unit configured to calculate a first evaluation value, indicating an adequacy of a color of the object visually perceived, based on the spectral distributions and the spectral reflectivity; and
a second calculating unit configured to calculate a second evaluation value, indicating how much an influence is given by the illuminating light to factors other than a visual sense, based on the spectral distributions,
wherein the light source control unit determines the emission intensities by which the first evaluation value and the second evaluation value satisfy a restraint condition determined beforehand.

2. The device according to claim 1, wherein the first evaluation value is a magnitude in a difference in appearances among plural regions included in the object.

3. The device according to claim 1, wherein the restraint condition is a condition in which the second evaluation value decreases with the first evaluation value being kept to be not less than a predetermined fixed value, or a condition in which the second evaluation value increases with the first evaluation value being kept to be not less than the fixed value.

4. The device according to claim 1, wherein the second evaluation value is an integral of a product of the spectral distributions and a action spectrum for melatonin suppression, or a value of a melatonin secretory inhibition prediction expression based on the responses of a cone, a rod, and a melanopsin-containing ganglion cell.

5. The device according to claim 1, wherein the estimation unit includes:
an imaging unit configured to capture an image of the object; and
an image processing unit configured to estimate the spectral reflectivity based on the image and the spectral distributions.

6. The device according to claim 5, wherein the imaging unit captures an image of the object through a variable filter of which spectral transmittance is changeable, and
the image processing unit estimates the spectral reflectivity based on the plural images, which are captured through the variable filter that is changed to the different spectral transmittances, and the spectral distributions.

7. The device according to claim 5, wherein the image processing unit estimates the spectral reflectivity based on the plural images captured under different spectral distributions of the light sources.

8. The device according to claim 1, wherein the estimation unit includes
- an input processing unit configured to accept an input value according to the spectral reflectivity, and estimate the spectral reflectivity according to the input value.

* * * * *